United States Patent
Ye et al.

(10) Patent No.: US 12,285,238 B2
(45) Date of Patent: Apr. 29, 2025

(54) BODY TEMPERATURE MEASURING PROBE, BODY TEMPERATURE MEASURING DEVICE AND BODY TEMPERATURE MEASURING METHOD

(71) Applicant: Shenzhen University, Guangdong (CN)

(72) Inventors: Jilun Ye, Guangdong (CN); Xu Zhang, Guangdong (CN)

(73) Assignee: SHEN ZHEN UNIVERSITY, Guangdong (CN)

( * ) Notice: Subject to any disclaimer, the term of this patent is extended or adjusted under 35 U.S.C. 154(b) by 984 days.

(21) Appl. No.: 17/276,588

(22) PCT Filed: Sep. 18, 2018

(86) PCT No.: PCT/CN2018/106344
§ 371 (c)(1),
(2) Date: Mar. 16, 2021

(87) PCT Pub. No.: WO2020/056612
PCT Pub. Date: Mar. 26, 2020

(65) Prior Publication Data
US 2022/0039663 A1    Feb. 10, 2022

(51) Int. Cl.
*A61B 5/01*    (2006.01)
*G01K 1/18*    (2006.01)
*G01K 13/20*   (2021.01)

(52) U.S. Cl.
CPC .............. *A61B 5/01* (2013.01); *G01K 1/18* (2013.01); *G01K 13/20* (2021.01)

(58) Field of Classification Search
CPC . A61B 5/01; A61B 5/015; G01K 1/18; G01K 13/20; G01K 13/223; G01J 5/0025; G01J 5/0011
See application file for complete search history.

(56) References Cited

U.S. PATENT DOCUMENTS

| | | | |
|---|---|---|---|
| 2014/0297215 A1* | 10/2014 | Meyerson | G01K 1/02 702/133 |
| 2018/0049646 A1* | 2/2018 | Ellis | A61B 5/0008 |
| 2019/0014990 A1* | 1/2019 | Franz | G01J 5/53 |

* cited by examiner

*Primary Examiner* — David J. McCrosky
*Assistant Examiner* — Meghan R Kumar
(74) *Attorney, Agent, or Firm* — DINSMORE & SHOHL LLP

(57) ABSTRACT

A body temperature measuring probe comprises a temperature sensor, a heating assembly and a position control assembly; the position control assembly controls contact or separation between the heating assembly and temperature sensor. A method for measuring body temperature comprises: starting the temperature sensor; preheating the body temperature measuring probe to a preset temperature range; once the body temperature measuring probe is preheated to the preset temperature range, separating the heating assembly from the temperature sensor, and only making the temperature sensor participate in a thermal equilibrium process of the body temperature measurement; the temperature sensor working to obtain body temperature measurement data. Once preheating of the temperature sensor is completed, the heating assembly and temperature sensor are separated so the temperature sensor may quickly reach a thermal equilibrium with a measured target; measuring time is thus shortened and high-precision body temperature measurement may be achieved.

6 Claims, 3 Drawing Sheets

BODY TEMPERATURE MEASURING PROBE, BODY TEMPERATURE MEASURING DEVICE AND BODY TEMPERATURE MEASURING METHOD

CROSS-REFERENCE TO RELATED APPLICATIONS

This application is the U.S. national stage of PCT/CN2018/106344 filed Sep. 18, 2018, which is incorporated herein by reference in its entirety.

TECHNICAL FIELD

The present application relates to the technical field of medical equipment, and in particular to a body temperature measuring probe, a body temperature measuring device and a body temperature measuring method.

BACKGROUND

In the applications of modern clinical surgery, intensive care, emergency treatment and outpatient service, body temperature is one of the key human body parameters; multi-parameter monitors and various types of thermometers involve body temperature measuring probes, body temperature measuring devices and body temperature measuring methods.

Body temperature measurements in the prior art usually adopt temperature sensors such as thermistors, pyroelectric sensors and the like to sense the body temperature. The body temperature measuring device adopting the infrared pyroelectric sensor has a short thermal equilibrium time, which can realize wireless or non-contact measurement, but the measurement error is relatively large.

In a body temperature measuring device using a thermistor, thermal equilibrium between a human body and a temperature sensor is established by contact of the temperature sensor with the human body, thereby achieving measurement of the body temperature. Temperature sensors using thermistors are accurate in monitoring, but require a long thermal equilibrium time.

In the prior art, the body temperature measuring probe is usually arranged at the end part of a cable of a monitor host machine or a thermometer host machine, thus cross-interference prevention of disinfection is troublesome, and it needs to be disinfected as a whole; in a contact type body temperature measuring device adopting a thermistor, a disposable protective sleeve is usually added, which can not only avoid cross-infection, but also avoid repeated disinfection of the entire cable, but the sleeve further increases the time for establishing thermal equilibrium in the measuring process, thereby increasing the measuring time; and the inconsistency of the sleeve can also increase measurement deviation and influence the measurement accuracy.

The normal body temperature of the human body is between 36-37° C. on average, it is not easy to achieve a balance between high precision and rapid measurement, among the prior art, in order to realize faster body temperature measurement, the temperature sensor has a preheating process during the measurement process, preheating the temperature sensor to a temperature range that is close to the normal temperature range of the human body avoids the process of adjusting the temperature sensor from the ambient temperature to close to the target measurement range, making the subsequent measurement process faster and more accurate.

SUMMARY OF THE APPLICATION

The present application aims to solve the technical problems of avoiding the defects of the above technical solutions and provides a body temperature measuring probe, device and method that can quickly establish thermal equilibrium.

The technical solution adopted by the present application for solving the technical problems is a body temperature measuring probe, comprising a temperature sensor for sensing temperature, a heating assembly for controlling preheating of the temperature sensor, and a position control assembly for controlling a position of the heating assembly; the position control assembly is connected with the heating assembly; the position control assembly controls contact or separation between the heating assembly and the temperature sensor.

The body temperature measuring probe further comprises a probe shell made of a thermal conductive material; the probe shell envelops the temperature sensor, the heating assembly and the position control assembly.

The body temperature measuring probe further comprises a probe interface for connecting the body temperature measuring probe to the outside; the probe interface comprises a mechanical interface for fixedly connecting the probe to an external cable, and an electrical interface for electrically connecting the probe to the outside.

The temperature sensor is a thermistor.

The position control assembly is an electromagnetic stroke control component which comprises an electromagnetic coil and a moving shaft, and one end of the moving shaft is fixedly connected with the heating assembly; and the electromagnetic coil generates an electromagnetic field through current therein, and a magnetic force of the electromagnetic field acts on the moving shaft to drive the heating assembly to move, so as to realize the contact or separation between the heating assembly and the temperature sensor.

The shape of the probe shell includes any one of a hemispherical shape, a semi-ellipsoidal shape, a conical shape, and a cylindrical shape.

The technical solution adopted by the present application for solving the technical problems can further be a body temperature measuring device comprising the body temperature measuring probe, wherein the body temperature measuring device comprises an analog signal processing module, a first driving module for driving a temperature sensor, a heating driving module for driving a heating assembly, a second driving module for driving a position control assembly and a main control module for controlling the body temperature measuring device; the body temperature measuring probe comprises a probe interface for connecting the body temperature measuring probe to the outside; the probe interface comprises an electrical interface for electrically connecting the body temperature measuring probe to the outside; the first driving module is electrically connected with the temperature sensor through the electrical interface and provides driving for the temperature sensor; the main control module is electrically connected with the heating driving module, and the heating driving module is electrically connected with the heating assembly through the electrical interface; the main control module is electrically connected with the second driving module, and the second driving module is electrically connected with the position control assembly through the electrical interface.

The temperature sensor in the body temperature measuring probe is a thermistor; the body temperature measuring device further comprises a calibration device for improving consistency of the thermistor in the body temperature measuring probe; and the calibration device comprises a calibration resistor controlled by the main control module.

The technical solution adopted by the present application for solving the technical problems can further be a body temperature measuring method based on the body temperature measuring probe, comprising: step 100: starting the temperature sensor; step 200: preheating the body temperature measuring probe to a preset temperature range; step 300: once the body temperature measuring probe is preheated to the preset temperature range, separating the heating assembly from the temperature sensor, and only making the temperature sensor participate in a thermal equilibrium process of the body temperature measurement; and step 400: the temperature sensor working to obtain body temperature measurement data.

In the step 100, first performing measurement to obtain an initial temperature value after starting the temperature sensor; the step 200 comprises the following sub-steps: step 210: determining whether the initial temperature value obtained in the step 100 is within the preset temperature range; if the initial temperature value is smaller than a lower limit of the preset temperature range, going to step 230; if the initial temperature value is greater than or equal to an upper limit of the preset temperature range, going to step 250; step 230: starting the heating assembly; and step 250: turning off the heating assembly.

The step 230 further comprises the following steps before starting the heating assembly: step 231: determining a connection state between the heating assembly and the temperature sensor; step 233: if the heating assembly and the temperature sensor are in a contact state, starting the heating assembly; and step 235: if the heating assembly and the temperature sensor are in a separation state, controlling movement of the heating assembly through the position control assembly to cause the heating assembly to get into contact with the temperature sensor, and then starting the heating assembly.

Compared with the prior art, the present application has the beneficial effects that: the connection state between the heating assembly and the temperature sensor is controlled by the position control assembly, the heating assembly can participate in the preheating process of the temperature sensor in the preheating state, can be separated from the temperature sensor after preheating is completed, and does not participate in subsequent measuring process of the temperature sensor, so that the temperature sensor can quickly reach thermal equilibrium with a measured object, the time to reach thermal equilibrium between the temperature sensor and the measured object is shortened, and high-precision body temperature measurement can be further quickly realized.

BRIEF DESCRIPTION OF THE DRAWINGS

in FIG. 2, the heating assembly 20 and the temperature sensor 10 are in a separation state; in FIG. 3, the heating assembly 20 and the temperature sensor 10 are in a contact state;

DETAILED DESCRIPTION OF EMBODIMENTS

Embodiments of the present application will be described in further detail below with reference to the accompanying drawings.

Figure 1:
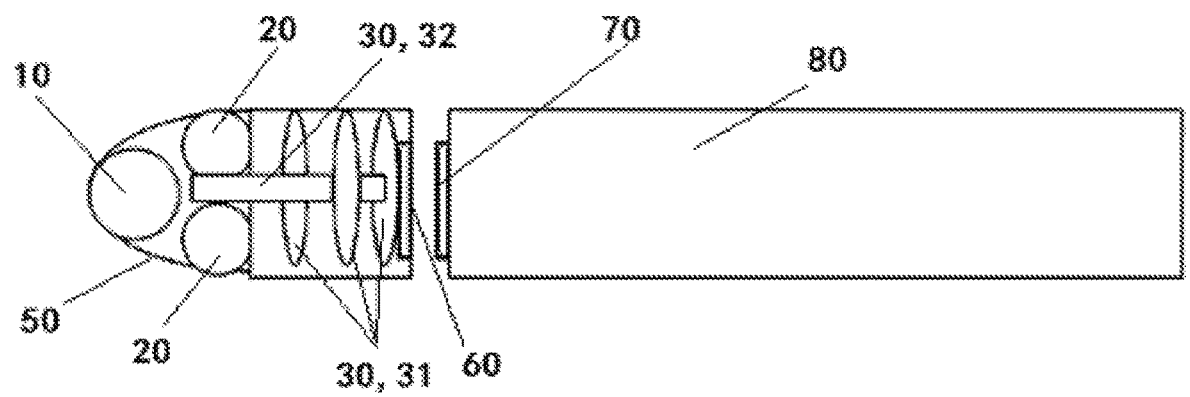
FIG. 1 is one of the structural schematic diagrams of a body temperature measuring probe.
Figure 2:
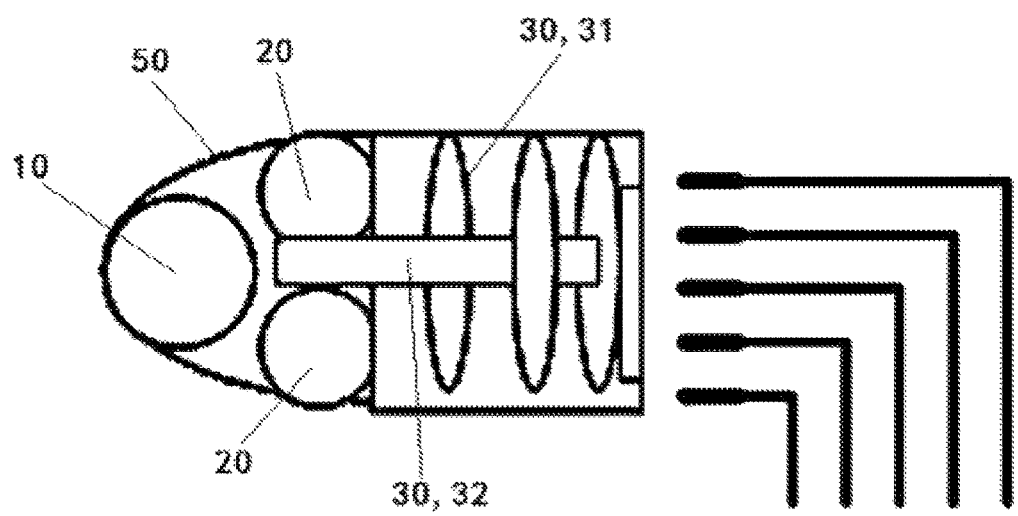
FIG. 2 and FIG. 3 are two structural schematic diagrams of the body temperature measuring probe.

In an embodiment of the body temperature measuring probe as shown in FIG. 1 and FIG. 2, the probe comprises a temperature sensor 10 for sensing temperature, a heating assembly 20 for controlling preheating of the temperature sensor, a position control assembly 30 for controlling a position of the heating assembly; the position control assembly is connected with the heating assembly; the position control assembly controls contact or separation between the heating assembly and the temperature sensor.

In an embodiment of the body temperature measuring probe as shown in FIG. 1 and FIG. 2, the probe further comprises a probe shell 50 made of a thermal conductive material; the probe shell envelops the temperature sensor 10, the heating assembly 20 and the position control assembly 30. The probe shell made of a thermal conductive material further accelerates the thermal equilibrium process in temperature measurement, thus it also shorten the measuring time and better achieve rapid temperature measurement.

In an embodiment of the body temperature measuring probe shown in FIG. 1 and FIG. 2, the probe further comprises a probe interface 60 for connecting the body temperature measuring probe to the outside, the probe interface 60 is used for mechanical connection and electrical connection to an external cable interface 70 and an external cable 80. The probe interface 60 comprises a mechanical interface for fixedly connecting the body temperature measuring probe to the external cable. In an embodiment of the body temperature measuring probe, not shown in the drawings, the probe interface comprises a mechanical interface for fixedly connecting the probe to an external cable, and an electrical interface for electrically connecting the probe to the outside. The electrical interface for electrically connecting the body temperature measuring probe to the outside at least comprises three electrical signal connecting terminals which are respectively used for transmission of a temperature sensor driving signal, a heating assembly driving signal and a position control assembly driving signal.

Figure 3:
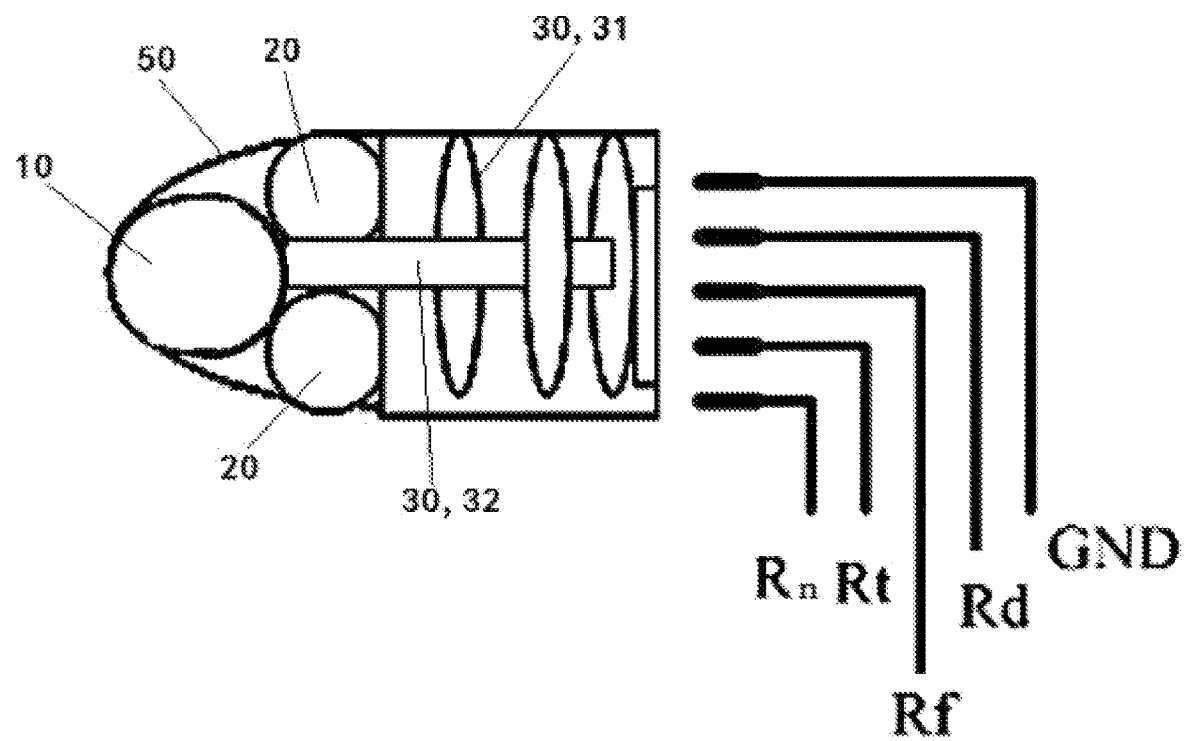

As shown in FIG. 2, the electrical interface of the body temperature measuring probe includes 5 electrical contacts, Rt, Rd, Rf and two GNDs, and as shown in FIG. 3, the electrical interface of the body temperature measuring probe includes 5 electrical contacts, Rt, Rd, Rf, Rn and one GND; the electrical interface realizes the electrical connection between the body temperature measuring probe and the main measuring system. The main measuring system may be a body temperature measuring device including a monitor, a thermometer, and the like.

As shown in FIG. 1 and FIG. 2, the body temperature measuring probe is enveloped by the probe shell, and is mechanically and electrically connected to the outside through the probe interface, so that the whole body temperature measuring probe can be conveniently replaced, and the thermal conductive material for manufacturing the probe shell comprises stainless steel or other materials with good thermal conductivity and convenience for disinfection, so that the independent body temperature measuring probe can be conveniently detached and independently disinfected at high temperature, and it is not necessary to disinfect the entire thermometer or together with the measuring cable or main equipment. The shell directly envelops the temperature sensor, and the body temperature measuring probe realizes the rapid measurement of the body temperature in a mode of directly contacting the human body.

As shown in FIG. 1 and FIG. 2, the movable connection between the heating assembly and the temperature sensor realizes contact and separation when necessary, so that only the temperature sensor participates in the thermal equilibrium process of the temperature measurement of the latter stage in the rapid body temperature measuring process, since the heating assembly does not participate in the heat exchange process of the last stage, the time required for reaching the thermal equilibrium is greatly shortened, thus solving the problem of long time for rapid body temperature measurement in the prior art.

The structure form of the probe which can be independently disinfected removes the sheath matched with the body temperature measuring probe in the prior art, so that the temperature sensor of the body temperature measuring probe is in more direct contact with the human body, and the contact area is larger, the periphery of the temperature sensor of the thermistor is enveloped by a semicircular stainless steel probe shell with excellent conductivity, so that the measuring result is more accurate; because no sheath is needed, it also avoids the measurement deviation caused by the inconsistent sheath in the rapid body temperature measurement in the prior art, and the measurement accuracy is further improved, and meanwhile, the problem of environmental pollution caused by a disposable sheath is also avoided.

As shown in FIG. 2 and FIG. 3, the temperature sensor is a thermistor type temperature measuring device, the heating assembly is used for accelerating the compensation of the difference between the temperature measuring device and the temperature to be measured, the position control assembly can control the contact or separation between the heating assembly and the temperature sensor, in FIG. 3, the heating assembly 20 and the temperature sensor 10 are in a contact state, and in FIG. 2, the heating assembly 20 and the temperature sensor 10 are in a separation state. The heating assembly is driven by direct current and the heating assembly is fixedly connected with the position control assembly; the position control assembly is an electromagnetic stroke control component, the electromagnetic stroke control component comprises an electromagnetic coil and a moving shaft, and one end of the moving shaft is fixedly connected with the heating assembly; when heating is required, the heating assembly is driven by the electromagnetic stroke device to be in contact with the thermistor, and the thermistor part is heated to an expected 35° C.+/−0.5° C. or other set temperature ranges; when the thermistor is heated to the expected temperature range, and the heating is stopped, and the heating assembly is separated from the thermistor through the electromagnetic stroke device, only the thermistor participates in the temperature exchange process of temperature measurement by contact with the human body, which prevents the heating device from also participating in the temperature exchange process, and reduces thermal capacity of temperature rise of the whole body temperature measuring probe.

Figure 4:
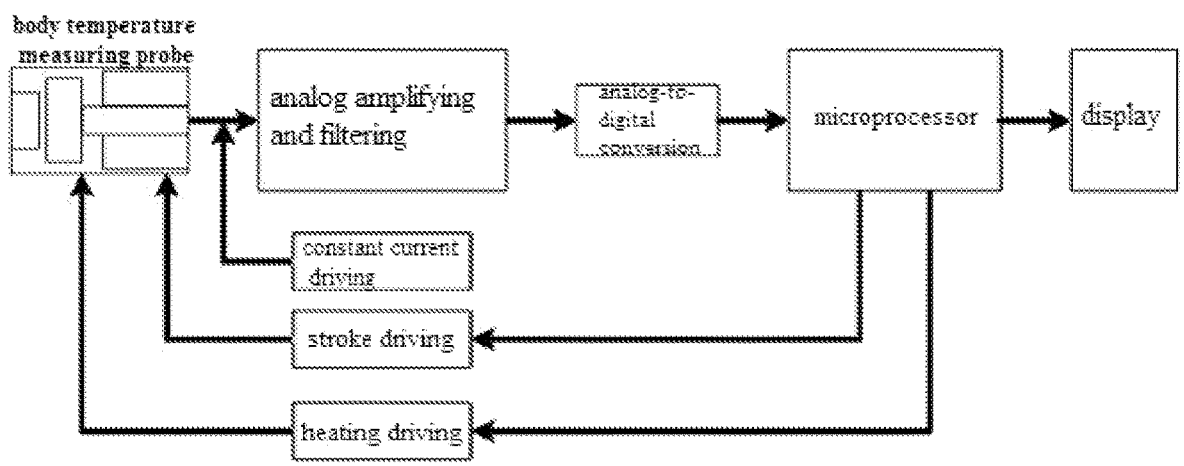
FIG. 4 is a schematic block diagram of a system of a body temperature measuring device.

In an embodiment of the body temperature measuring device shown in FIG. 4, the body temperature measuring device comprises an analog signal processing module, a first driving module for driving a temperature sensor, a heating driving module for driving a heating assembly, a second driving module for driving a position control assembly and a main control module for controlling the body temperature measuring device; the body temperature measuring probe comprises a probe interface for connecting the body temperature measuring probe to the outside; the probe interface comprises an electrical interface for electrically connecting the body temperature measuring probe to the outside; the first driving module is electrically connected with the temperature sensor through the electrical interface and provides driving for the temperature sensor, and the first driving module is shown as a constant current driving module in FIG. 4; the main control module is electrically connected with the heating driving module, and the heating driving module is electrically connected with the heating assembly through the electrical interface; the main control module is electrically connected with the second driving module, and the second driving module is electrically connected with the position control assembly through the electrical interface, and the second driving module is shown as a stroke driving module in FIG. 4.

The heating driving module can be based on circuit components such as a PWM pin, an I/O interface and a corresponding CMOS tube and the like of the main control module, and realizes the preheating function aiming at the rapid body temperature measurement through a software algorithm in the main control module. Wherein, the heating assembly can adopt a resistor or a thermal conductive film, and the control of the heating process is realized through the PWM control cooperation of the main control module.

The second driving module for driving the position control assembly can realize the control of the position control assembly based on circuit components such as a PWM pin, an I/O interface and a corresponding CMOS tube and the like of the main control module. The position control assembly is an electromagnetic stroke component, the electromagnetic stroke component comprises an electromagnetic coil 31 and a moving shaft 32, and one end of the moving shaft is fixedly connected with the heating assembly; the electromagnetic coil generates an electromagnetic field through current therein, and a magnetic force of the electromagnetic field acts on the moving shaft to drive the heating assembly to move, so as to realize the contact or separation between the heating assembly and the temperature sensor.

The moving shaft 32 can be a spring, and the electromagnetic component realizes a 2-5 mm stroke change of the spring through the electromagnetic force of the electromagnetic field so as to achieve the contact and separation between the heating part and the measuring part, reduce the thermal capacity of the assembly participating in the heat exchange of subsequent temperature measurement, and only the temperature sensor and the shell enveloping the temperature sensor participate in the heat exchange process of other stages after the preheating stage.

In an embodiment of the body temperature measuring device shown in FIG. 4, the analog signal processing module includes an analog amplifying and filtering processing module and an analog-to-digital conversion module, so as to amplify, filter and digitize the analog signal output by the temperature sensor, the digitized temperature signal is input to the main control module for subsequent calculations, and the main control module includes a microprocessor and related circuits. The main control module comprises a microprocessor which is an operation platform of software and related algorithms; the body temperature measuring device can also comprise a necessary power supply display module and the like. The power supply display module comprises a power supply for supplying power to the device and a display for human-machine interaction and temperature measurement data display.

In other embodiments of the body temperature measuring device not shown in the drawings, the body temperature measuring device can be divided into a temperature measuring module, a heating and stroke control module, a main control module and a power supply display module. The temperature measuring module comprises an analog amplifying and filtering module, an analog-to-digital conversion module and a constant current driving module of the temperature sensor; the temperature measuring module and the software algorithm in the main control module cooperate to realize the rapid measurement of the body temperature.

An embodiment of the body temperature measuring method comprises:

Step 100: starting the temperature sensor to start measuring and obtaining an initial temperature value;

Step 200: preheating the body temperature measuring probe to a preset temperature range;

Step 300: once the body temperature measuring probe is preheated to the preset temperature range, separating the heating assembly from the temperature sensor, and only making the temperature sensor participate in a thermal equilibrium process of the body temperature measurement; and obtaining body temperature measurement data.

The step 200 comprises the following sub-steps: step 210: determining whether the initial temperature value obtained in the step 100 is within the preset temperature range; if the initial temperature value is smaller than a lower limit of the preset temperature range, going to step 230; if the initial temperature value is greater than or equal to an upper limit of the preset temperature range, going to step 250; step 230: starting the heating assembly; and step 250: turning off the heating assembly.

The step 230 further comprises the following steps before starting the heating assembly:

Step 231: determining a connection state between the heating assembly and the temperature sensor;

Step 233: if the heating assembly and the temperature sensor are in a contact state, starting the heating assembly;

Step 235: if the heating assembly and the temperature sensor are in a separation state, controlling movement of the heating assembly through the position control assembly to cause the heating assembly to get into contact with the temperature sensor, and then starting the heating assembly.

Figure 5:
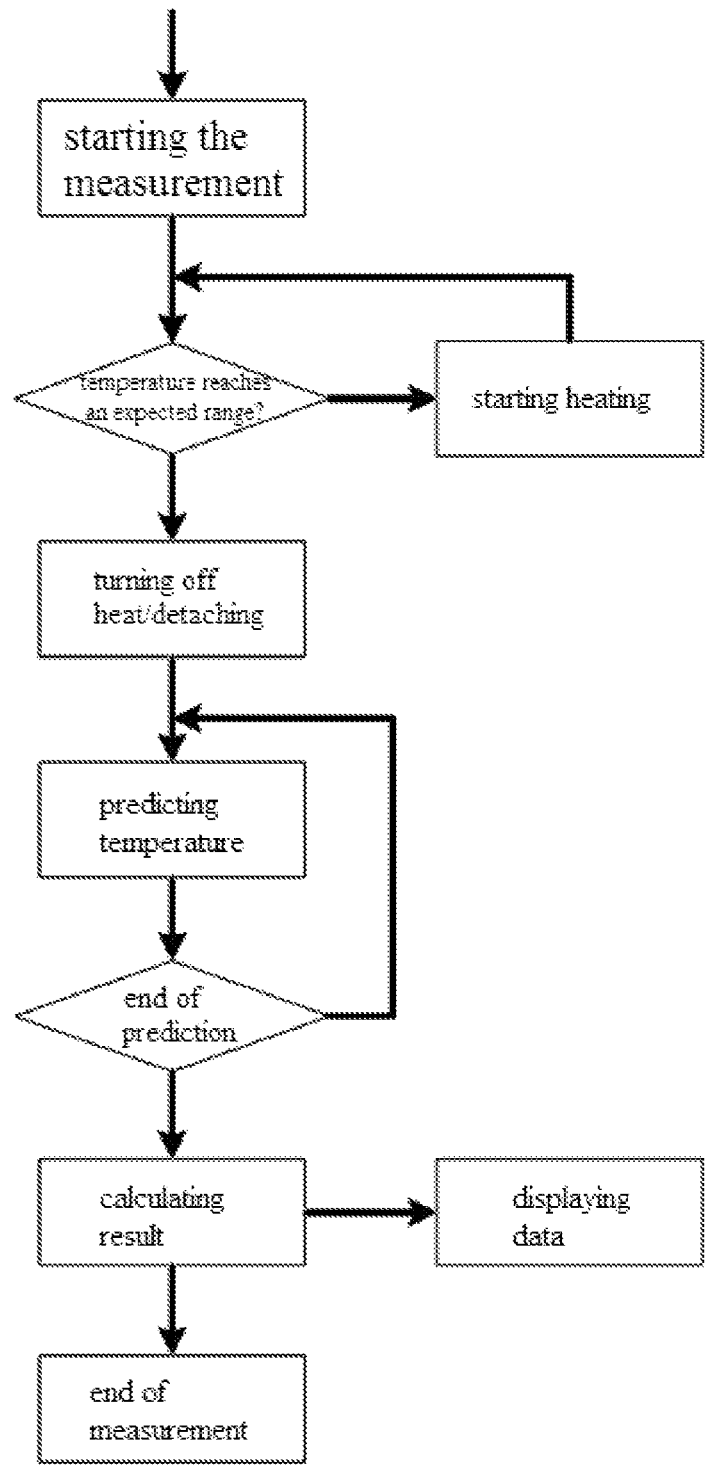
FIG. 5 is a schematic flowchart diagram of a preferred embodiment of a body temperature measuring method.

In the flowchart diagram of the body temperature measuring method as shown in FIG. 5:

First step: firstly, starting the measurement;

Second step: determining whether the initial temperature reaches an expected range, if it does not reach the expected range, starting the heating assembly to start heating until the temperature reaches the expected range;

Third step: turning off the heating assembly or detaching the heating assembly from the temperature sensor;

Fourth step: performing rapid body temperature prediction, and outputting a prediction result;

Fifth step: determining whether the prediction result can be used for subsequent calculations, if so, entering the sixth step, and if not, returning to the step of temperature prediction in the fourth step;

Sixth step: calculating the measurement result and outputting the measurement data.

The movable mode of the heating component is adopted, the heating assembly and the temperature sensor are in direct contact to rapidly finish the preheating process in the preheating stage of the rapid body temperature sensor, the heating assembly and the temperature sensor are separated in the measuring stage after the rapid body temperature sensor finishes the preheating stage, the thermal capacity of a part participating in measurement is reduced, only the temperature sensor and a necessary shell part participate in temperature exchange, so as to achieve faster response of the temperature sensor.

Compared with the prior art, the rapid body temperature measuring device and system designed by the present application overcome the defects of the existing body temperature measuring device in the aspects of measuring time, measuring precision, environmental pollution and the like, improve the measuring precision and the usability of an application system, the measuring time is estimated to be less than 10 seconds, with an accuracy of +/−0.1° C., and reduce environmental pollution. It has excellent clinical application value, is a necessary monitoring instrument for departments of outpatient services, community clinics and the like, it can completely replace similar imported measurement technologies in terms of measurement functions and key indexes, and can generate obvious economic benefits.

The above description is only embodiments of the present application, and is not intended to limit the scope of the present application, any transformation of equivalent structures or equivalent processes performed by the specification and the attached drawings of the present application, or directly or indirectly applied to other related technical fields, are likewise included in the scope of the present application.

The invention claimed is:

1. A body temperature measuring probe, comprising:
a temperature sensor for sensing temperature, a heating assembly for controlling preheating of the temperature sensor, and a position control assembly for controlling a position of the heating assembly;
the position control assembly is connected with the heating assembly; the position control assembly controls contact or separation between the heating assembly and the temperature sensor;
the position control assembly is an electromagnetic stroke control component which comprises an electromagnetic coil and a moving shaft, and one end of the moving shaft is fixedly connected with the heating assembly; and
the electromagnetic coil generates an electromagnetic field through current therein, and a magnetic force of the electromagnetic field acts on the moving shaft to drive the heating assembly to move, so as to realize the contact or separation between the heating assembly and the temperature sensor.

2. The body temperature measuring probe of claim 1, further comprising:
a probe shell made of a thermal conductive material;
the probe shell envelops the temperature sensor, the heating assembly and the position control assembly.

3. The body temperature measuring probe of claim 1, further comprising:
a probe interface for connecting the body temperature measuring probe to an external cable and an external device or system;
the probe interface comprises a mechanical interface for fixedly connecting the probe to the external cable, and an electrical interface for electrically connecting the probe to the external device or system.

4. The body temperature measuring probe of claim 1, wherein the temperature sensor is a thermistor.

5. A body temperature measuring device based on the body temperature measuring probe of claim 1, wherein:

the body temperature measuring device comprises an analog signal processing module, a first driving module for driving a temperature sensor, a heating driving module for driving a heating assembly, a second driving module for driving a position control assembly and a main control module for controlling the body temperature measuring device;

the body temperature measuring probe comprises a probe interface for connecting the body temperature measuring probe to an external cable and an external device or system; the probe interface comprises an electrical interface for electrically connecting the body temperature measuring probe to the external device or system;

the first driving module is electrically connected with the temperature sensor through the electrical interface and provides driving for the temperature sensor;

the main control module is electrically connected with the heating driving module, and the heating driving module is electrically connected with the heating assembly through the electrical interface; and the main control module is electrically connected with the second driving module, and the second driving module is electrically connected with the position control assembly through the electrical interface.

6. The body temperature measuring device of claim 5, wherein:

the temperature sensor in the body temperature measuring probe is a thermistor;

the body temperature measuring device further comprises a calibration device for improving consistency of the thermistor in the body temperature measuring probe; and the calibration device comprises a calibration resistor controlled by the main control module.

\* \* \* \* \*